(12) United States Patent
Korte et al.

(10) Patent No.: US 8,575,366 B2
(45) Date of Patent: Nov. 5, 2013

(54) METHOD FOR PRODUCING 2-HALOGENOMETHYLPHENYL ACETIC ACID DERIVATIVES

(75) Inventors: Alexander Korte, Neustadt (DE); Mark Alan Kearns, Wake Forest, NC (US); Jonathan O. Smith, Quincy, IL (US); Gunter Lipowsky, Ladenburg (DE); Willi Bieche, Erpolzheim (DE)

(73) Assignee: BASF SE, Ludwigshafen (DE)

(*) Notice: Subject to any disclaimer, the term of this patent is extended or adjusted under 35 U.S.C. 154(b) by 13 days.

(21) Appl. No.: 13/147,704

(22) PCT Filed: Feb. 1, 2010

(86) PCT No.: PCT/EP2010/051144
§ 371 (c)(1),
(2), (4) Date: Aug. 3, 2011

(87) PCT Pub. No.: WO2010/089267
PCT Pub. Date: Aug. 12, 2010

(65) Prior Publication Data
US 2011/0295022 A1    Dec. 1, 2011

(30) Foreign Application Priority Data
Feb. 5, 2009 (EP) ................................ 08172487

(51) Int. Cl.
*C07D 311/02* (2006.01)
*C07C 229/00* (2006.01)

(52) U.S. Cl.
USPC ............................................. 549/288; 560/35

(58) Field of Classification Search
USPC ............................................. 549/288; 560/35
See application file for complete search history.

(56) References Cited

U.S. PATENT DOCUMENTS

| | | | |
|---|---|---|---|
| 4,829,085 A | 5/1989 | Wenderoth et al. | |
| 5,221,762 A | 6/1993 | Wingert et al. | |
| 5,446,199 A | 8/1995 | Isak et al. | |
| 5,504,249 A | 4/1996 | Isak et al. | |
| 5,585,513 A * | 12/1996 | Matthews et al. | 560/60 |
| 5,780,665 A | 7/1998 | Isak et al. | |
| 5,856,560 A | 1/1999 | Bayer et al. | |
| 7,034,181 B1 | 4/2006 | Goetz et al. | |
| 7,947,734 B2 | 5/2011 | Liu et al. | |
| 2005/0113597 A1 | 5/2005 | Mayer et al. | |

FOREIGN PATENT DOCUMENTS

| | | |
|---|---|---|
| CN | 101139308 | 3/2008 |
| CN | 101205187 | 6/2008 |
| DE | 19959066 | 5/2001 |
| DE | 10007695 | 8/2001 |
| EP | 0 253 213 | 1/1988 |
| EP | 0 254 426 | 1/1988 |
| EP | 0 398 692 | 11/1990 |
| EP | 0 493 711 | 7/1992 |
| EP | 0 619 300 | 10/1994 |
| EP | 0 676 389 | 10/1995 |
| WO | WO 93/07116 | 4/1993 |
| WO | WO 95/34526 | 12/1995 |
| WO | WO 96/16023 | 5/1996 |
| WO | WO 97/48671 | 12/1997 |
| WO | WO 01/42182 | 6/2001 |
| WO | WO 01/42185 | 6/2001 |
| WO | WO 03/072538 | 9/2003 |
| WO | WO 2007/000098 | 1/2007 |

OTHER PUBLICATIONS

International Search Report prepared in International Application No. PCT/EP2010/051144, filed Feb. 1, 2010.

International Preliminary Report on Patentability from corresponding International Application No. PCT/EP2010/051144, filed Feb. 1, 2010.

Ahmad, I., et al., "A convenient entry into the rhoeadan skeleton. Total synthesis of (±)-*cis*-alpinigenine[1]", Canadian Journal Chemistry, (1982), pp. 2678-2686, vol. 60, No. 21, Search Report.

* cited by examiner

*Primary Examiner* — Nizal Chandrakumar
(74) *Attorney, Agent, or Firm* — Brinks Hofer Gilson & Lione

(57) ABSTRACT

The present invention relates to a process for producing 2-halogenomethylphenyl acetic acid derivatives.

10 Claims, No Drawings

METHOD FOR PRODUCING 2-HALOGENOMETHYLPHENYL ACETIC ACID DERIVATIVES

This application is a National Stage application of International Application No. PCT/EP2010/051144 filed Feb. 1, 2010, the entire contents of which is hereby incorporated herein by reference. This application also claims priority under 35 U.S.C. §119 to European Patent Application No. 08172487.4 filed Feb. 5, 2009, the entire contents of which is hereby incorporated herein by reference.

The present invention relates to a process for producing 2-halogenomethylphenyl acetic acid derivatives of formula I

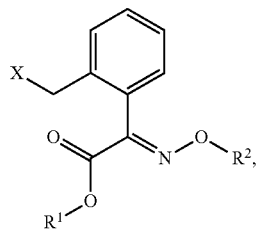

(I)

wherein X is chlorine or bromine;
$R^2$ is hydrogen, methyl or ethyl; and
$R^1$ is methyl, ethyl, i-propyl or n-propyl; said process comprising cleavage of an alkyloxime of formula II

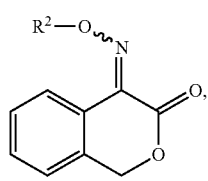

(II)

wherein $R^2$ is methyl or ethyl in the presence of an alcohol of formula III

$R^1$—OH (III), wherein $R^1$ is methyl, ethyl, i-propyl or n-propyl; and a halogenating agent selected from the group consisting of thionyl halide, oxalyl halide and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid.

2-Halogenomethylphenyl acetic acid derivatives are important intermediates for the preparation of agrochemically active compounds or microbiocides, e.g. in strobilurine synthesis. For example, the strobilurines dimoxystrobin, trifloxystrobin, kresoxim-methyl and orysastrobin can be easily produced by using these compounds.

The terms "dimoxystrobin", "trifloxystrobin", "kresoxim-methyl" and "orysastrobin" are the ISO names of certain agrochemically active compounds or microbiocides, analogously to INN names of pharmaceutically active substances. The ISO names designate unambiguously a compound with a certain structure. The ISO names of the compounds, their structure and their IUPAC names respectively CAS names can be found e.g. on http://www.alanwood.net/pesticides/, or in "The Pesticide Manual", 14$^{th}$Edition, 2006 The British Crop Production Council. The respective substance can be on the market under a variety of trademark names.

Furthermore, 2-halogenomethylphenyl acetic acid derivatives can be also used as intermediates in the syntheses of substituted p-trifluoromethyl phenyl ethers, which are compounds with insecticidal activity (WO 2007/000098 A1 and CN 101205187 A).

Currently published methods for the production of 2-halogenomethylphenyl acetic acid derivatives describe a route based on phthalides of formula A

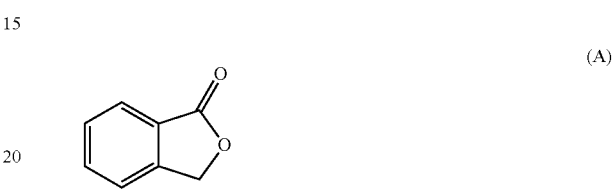

(A)

(an overview is given in CN 101139308, details for the respective single steps of the synthesis are, for example disclosed in DE 10007695 A, DE 19959066, WO 01/42182, WO 01/42185, EP 0676389 A, EP 0619300 A, WO 96/16023, EP 0493711A, EP 254 426 A and EP 253213 A). The synthesis contains a ring-opening step of the phthalide of formula A with thionyl chloride at temperatures >100° C. followed by a reaction with toxic sodium cyanide.

Object of the present invention was to provide an efficient and/or short production route suitable for large scale synthesis, especially a production route to 2-halogenomethylphenyl acetic acid derivatives.

Further object of the present invention was to provide a production route, which can be based on educts (starting materials), which are less toxic than those used in currently existing routes.

The object was solved by a process for producing 2-halogenomethylphenyl acetic acid derivatives of formula I, which is based on 3-isochromanone.

Isochromanone-based syntheses for 2-(chloro- or bromomethyl)phenylacetates, which may serve as intermediates for agrochemicals, is mentioned in the art (see WO 97/48671). However, the processes described therein do not disclose the specific process of the present invention.

WO 93/07116 describes an isochromanone based synthesis of 2-hydroxymethylphenyl acetic acid derivatives.

The present invention relates to a process for producing 2-halogenomethylphenyl acetic acid derivatives of formula I

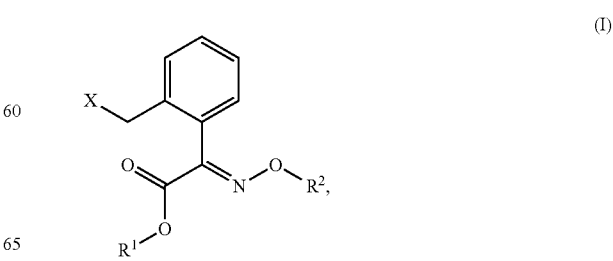

(I)

wherein X is chlorine or bromine;
R² is hydrogen, methyl or ethyl; and
R¹ is methyl, ethyl, i-propyl or n-propyl; said process comprising cleavage of an alkyloxime of formula II

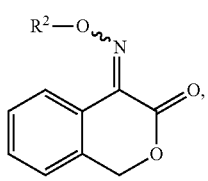
(II)

wherein R² is hydrogen, methyl or ethyl; in the presence of an alcohol of formula III

R¹—OH    (III), wherein R¹ is methyl, ethyl, i-propyl or n-propyl; and a halogenating agent selected from the group consisting of thionyl halide, oxalyl halides and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid.

The term i-propyl is understood to be identical to iso-propyl (—CHMe₂). N-propyl is understood to be the linear propyl radical group.

The compound of formula I is a mixture of E/Z isomers. Preferably, the E isomer is present ≥85% E isomer and ≤15% Z isomer, more preferably ≥90% E isomer and ≤10% Z isomer, most preferably ≥95% E isomer and ≤5% Z isomer.

Preferably, R¹ is methyl or ethyl, more preferably methyl.
Preferably, X is chlorine.
Preferably, R² methyl or ethyl, more preferably methyl.
Particular preference is given to compounds of formula I listed in table I

| No | X | R¹ | R² |
|---|---|---|---|
| I-1 | chlorine | methyl | methyl |
| I-2 | chlorine | ethyl | methyl |
| I-3 | chlorine | methyl | hydrogen |
| I-4 | chlorine | ethyl | hydrogen |
| I-5 | bromine | methyl | methyl |
| I-6 | bromine | ethyl | methyl |
| I-7 | bromine | methyl | hydrogen |
| I-8 | bromine | ethyl | hydrogen |

In this subset, compounds I-1, I-2, I-3 and I-4 are preferred, and I-1 and I-2 are most preferred.

To achieve the preferred combinations, the skilled artisan will use the respective educts (starting materials) as outlined below.

Suitable thionyl halides are, for example thionyl chloride or thionyl bromide. Suitable oxalyl halides are oxalyl chloride or oxalyl bromide.

Suitable mixtures are mixtures of thionyl chloride and hydrochloric acid, thionyl bromide and hydrobromic acid, oxalyl chloride and hydrochloric acid, oxalyl bromide and hydrobromic acid.

The ratio of thionyl halide (or oxalyl halides) and respective acid is 1000:1 to 1:10, preferably 1:1 to 1:10, more preferably 1:3 to 1:5.

Preferred halogenating agents are thionyl halide or a mixture of thionyl halide and hydrochloric or hydrobromic acid.

For chlorination, thionyl chloride or a mixture of thionyl chloride and hydrochloric acid is preferred.

For bromination, thionyl bromide or a mixture of thionyl bromide and hydrobromic acid is preferred.

If the halogenating agent is thionyl halide or an oxalyl halide the molar ratio of compound of formula II and the halogenating agent is preferably 1:1 to 1:20, more preferably 1:3 to 1:15, most preferably 1:5 to 1:10.

If a mixture of thionyl halide (or oxalyl halide) and respective acid is used, the molar ratio of compound of formula II and thionyl halide (or oxalyl halides) is 1:1 to 1:20, more preferably 1:3 to 1:15, most preferably 1:3 to 1:5.

Preferably, the molar ratio of the compound of formula II and the alcohol is 1:10 to 1:100, preferably 1:10 to 1:60, more preferably 1:20 to 1:50.

Optionally, the reaction mixture can further comprise an inert organic solvent. Useful solvents include aromatic (halogenated) hydrocarbons, e.g. benzene, toluene, xylene, chlorobenzene, dichlorobenzene, bromobenzene and benzotrifluoride; aliphatic (halogenated) hydrocarbons, e.g. pentane, heptane, dichloromethane, chloroform, 1,2-dichloroethane and carbon tetrachloride; cycloaliphatic hydrocarbons, e.g. cyclohexane and cyclopentane; ethers, e.g. dimethoxyethane, diethyl ether and di-isopropyl ether; esters, e.g. ethyl acetate and butyl acetate and polar aprotic solvents such as dimethylformamide, N-methylpyrrolidone, dimethylsulfoxide. Also mixtures of these solvents may be used. Preferred solvents include aromatic (halogenated) hydrocarbons, e.g. benzene, toluene, xylene, chlorobenzene and dichlorobenzene; aliphatic (halogenated) hydrocarbons such as e.g. dichloromethane, chloroform, 1,2-dichloroethane and carbon tetrachloride and polar aprotic solvents such as dimethylformamide, N-methylpyrrolidone. Also mixtures of these solvents may be used.

The reaction pressure is customarily from 0 to 100 bar. Preference is given to carrying out the reaction under atmospheric pressure. If the reaction is carried out under atomospheric pressure, the reaction temperature is customarily from −20 to 100° C., preferably from −10 to 40° C., more preferably from −10 to 30° C.

The compounds of formula II, wherein R² is methyl or ethyl, can be obtained by reacting an oxime of formula IV

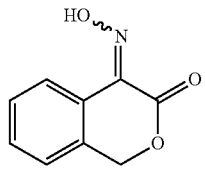
IV according to methods known in the art, for example with an alkylating agent and a base in an inert organic solvent.

Suitable alkylating agents are widely known to the skilled artisan. Examples of suitable alkylating agents are dimethylsulfate, methyliodide, methylbromide, methylchloride, diazomethane and diethylsulfate, ethyliodide, ethylbromide, ethylchlorid. Preferred alkylating agents are dimethylsulfate and methyliodide, more preferably dimethylsulfate.

Suitable bases are widely known to the skilled artisan. Examples of suitable bases include, but are not limited to potassium carbonate, sodium carbonate, potassium hydroxide, sodium hydroxide. Preferred bases are potassium carbonate and sodium carbonate, more preferably potassium carbonate. Useful solvents include aromatic (halogenated)

hydrocarbons, e.g. benzene, toluene, xylene, chlorobenzene, dichlorobenzene, bromobenzene and benzotrifluoride; aliphatic (halogenated) hydrocarbons, e.g. pentane, heptane, dichloromethane, chloroform, 1,2-dichloroethane and carbon tetrachloride; cycloaliphatic hydrocarbons, e.g. cyclohexane and cyclopentane; ethers, e.g. dimethoxyethane, diethyl ether and di-isopropyl ether; esters, e.g. ethyl acetate and butyl acetate and polar aprotic solvents such as dimethylformamide, N-methylpyrrolidone, dimethylsulfoxide. Also mixtures of these solvents may be used. Preferred solvents include aromatic (halogenated) hydrocarbons, e.g. benzene, toluene, xylene, chlorobenzene and dichlorobenzene; aliphatic (halogenated) hydrocarbons such as e.g. dichloromethane, chloroform, 1,2-dichloroethane and carbon tetrachloride and polar aprotic solvents such as dimethylformamide, N-methylpyrrolidone. Also mixtures of these solvents may be used.

To achieve high yields, it is preferred to use toluene as solvent.

The reaction pressure is customarily from 0 to 6 bar. Preference is given to carrying out the reaction under atmospheric pressure. If the reaction is carried out under atomospheric pressure, the reaction temperature is customarily from 0 to 100° C., preferably from 0 to 40° C., more preferably from 5 to 25° C.

The invention comprises also a process for producing 2-halogenomethylphenyl acetic acid derivatives of formula I as described herein, wherein X is chlorine or bromine;

$R^2$ is hydrogen, methyl or ethyl; and $R^1$ is methyl, ethyl, i-propyl or n-propyl;

said process comprising cleavage of an alkyloxime of formula II, wherein $R^2$ is methyl or ethyl, in the presence of an alcohol $R^1$—OH of formula III, wherein $R^1$ is methyl, ethyl, i-propyl or n-propyl, and a halogenating agent selected from the group consisting of thionyl halide, oxalyl halide and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid, further comprising a process as described herein for reacting an oxime of formula IV to an alkyl oxime of formula II, in which the compounds of formula II, wherein $R^2$ is methyl or ethyl, are obtained by reacting an oxime of formula IV with an alkylating agent and a base in an inert organic solvent, wherein the inert organic solvent is preferably toluene.

The compounds of formula IV can be obtained by a process comprising a) reacting 3-isochromanone of formula V

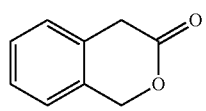

V with a nitrosating agent in presence of an alcohol and a base.

b) after completion of the reaction adjusting the pH to a pH≤3, preferably pH≤1.

Preferred alcohols are methanol, ethanol, propanol or i-propanol more preferably methanol or ethanol, most preferably methanol.

Suitable bases include, but are not limited to alcoholates. Preferred alcoholates are $Na^+$, $Li^+$ or $K^+$ alcoholates, preferably the corresponding $Na^+$ or $K^+$ alcoholates, most preferably $Na^+$ alcoholates.

More preferably, the alcoholate corresponds to the alcohol, preferred embodiments are $Na^+$ or $K^+$ $CH_3O^-$/$HOCH_3$
$Na^+$ or $K^+$ $CH_3CH_2O^-$/HO $CH_2CH_3$
$Na^+$ or $K^+$ $CH_3CH_2CH_2O^-$/HO $CH_2CH_2CH_3$
$Na^+$ or $K^+$ $(CH_3)_2CH_2O^-$/$HOCH_2(CH_3)_2$ more preferably $Na^+$ or $K^+$ $CH_3O^-$/$HOCH_3$
$Na^+$ or $K^+$ $CH_3CH_2O^-$/HO $CH_2CH_3$ most preferably $Na^+$ or $K^+$ $CH_3O^-$/$HOCH_3$ utmost preferably $Na^+$ $CH_3O^-$/$HOCH_3$ The pH adjustment is made by a suitable acid with a $pK_a \le 0$, preferably with a suitable mineral acid (e.g. hydrochloric acid, hydrobromic acid, sulfuric acid), more preferably with hydrochloric acid.

Suitable nitrosating agents are for example alkyl nitrites such as n-butyl nitrite, tert-butyl nitrite, iso-butyl nitrite, n-pentyl nitrite and iso-pentyl nitrite.

The reaction pressure is customarily from 0 to 6 bar. Preference is given to carrying out the reaction under atmospheric pressure. If the reaction is carried out under atmospheric pressure, the reaction temperature is customarily from 0 to 100° C., preferably from 10 to 40° C., more preferably from 15 to 30° C.

The invention comprises also a process for producing 2-halogenomethylphenyl acetic acid derivatives of formula I as described herein, wherein X is chlorine or bromine;

$R^2$ is hydrogen, methyl or ethyl; and $R^1$ is methyl, ethyl, i-propyl or n-propyl;

said process comprising cleavage of an alkyloxime of formula II, wherein $R^2$ is methyl or ethyl, in the presence of an alcohol $R^1$—OH of formula III, wherein $R^1$ is methyl, ethyl, i-propyl or n-propyl, and a halogenating agent selected from the group consisting of thionyl halide, oxalyl halide and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid, further comprising a process as described herein for reacting 3-isochromanone of formula V to an oxime of formula IV, in which a) 3-isochromanone of formula V is reacted with a nitrosating agent in presence of an alcohol and a base, and b) after completion of the reaction the pH is adjusted to a pH≤3, preferably pH≤1.

The present invention also comprises the use of 3-isochromanone of formula V for the production of 2-halogenomethylphenyl acetic acid derivatives of formula I. The gist of the invention is the provision of a synthesis route to compounds of formula I as defined herein (i.e. having a methoxyimino group), starting from 3-isochromanone of formula V.

WO 97/48671 discloses the cleavage of 3-isochromanone of formula V to 2-halogenomethylphenyl acetic acid derivatives of formula I':

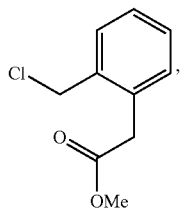

(I')

The compounds of formula I' disclosed in WO 97/48671 lack the methoxyimino group which is characteristic for the compounds of formula I according to the present invention. Although WO 97/48671 claims that the compounds of formula I' would be suitable for the synthesis of strobilurin type fungicides, for which a generic formula is given, WO 97/48671 fails to disclose how the methoxyimino group may be introduced into the compound.

If compounds of formula I' are subjected to the oximation step, this does not lead to the desired oxime product in sufficient yield, but only a complex mixture is obtained, making it impossible to proceed with the alkylation step. WO 97/48671 does therefore not put the person skilled in the art in the position to access compounds of formula I of present invention, starting from 3-isochromanone.

3-Isochromanone of formula V does not have any further functional groups and may therefore be easily cleaved. Surprisingly, it has been found that the compounds of formula II according to the present invention can be cleaved to compounds of formula I, in spite of their sensitive substituent(s).

In a preferred embodiment, the invention comprises the use of 3-isochromanone of formula V for the production of 2-halogenomethylphenyl acetic acid derivatives of formula I, which includes cleavage of an alkyloxime of formula II

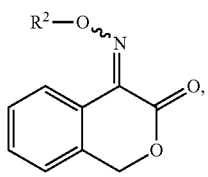

(II)

wherein
$R^2$ is methyl or ethyl;
in the presence of an alcohol of formula III

R$^1$—OH (III), wherein $R^1$ is $R^1$ is methyl, ethyl, n-propyl or i-propyl;
and a halogenating agent selected from the group consisting of thionyl halide, oxalyl halides and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid.

In a further embodiment, the 2-halogenomethylphenyl acetic acid derivatives of formula I, wherein $R^2$ is methyl or ethyl, can be produced based on 2-halogenomethylphenyl acetic acid derivatives of formula I, wherein $R^2$ is hydrogen, by alkylating compounds of formula I, wherein $R^2$ is hydrogen, in an inert organic solvent. Suitable alkylating agents are widely known to the skilled artisan. Examples of suitable alkylating agents are dimethylsulfate, methyliodide, methylbromide, methylchloride, diazomethane and diethylsulfate, ethyliodide, ethylbromide, ethylchloride. Preferred alkylating agents are dimethylsulfate and methyliodide, more preferably dimethylsulfate.

Suitable bases are widely known to the skilled artisan. Examples of suitable bases include, but are not limited to potassium carbonate, sodium carbonate, potassium hydroxide, sodium hydroxide. Preferred bases are potassium carbonate and sodium carbonate, more preferably potassium carbonate. Useful solvents include aromatic (halogenated) hydrocarbons, e.g. benzene, toluene, xylene, chlorobenzene, dichlorobenzene, bromobenzene and benzotrifluoride; aliphatic (halogenated) hydrocarbons, e.g. pentane, heptane, dichloromethane, chloroform, 1,2-dichloroethane and carbon tetrachloride; cycloaliphatic hydrocarbons, e.g. cyclohexane and cyclopentane; ethers, e.g. dimethoxyethane, diethyl ether and di-isopropyl ether; esters, e.g. ethyl acetate and butyl acetate and polar aprotic solvents such as dimethylformamide, N-methylpyrrolidone, dimethylsulfoxide. Also mixtures of these solvents may be used. Preferred solvents include aromatic (halogenated) hydrocarbons, e.g. benzene, toluene, xylene, chlorobenzene and dichlorobenzene; aliphatic (halogenated) hydrocarbons such as e.g. dichloromethane, chloroform, 1,2-dichloroethane and carbon tetrachloride and polar aprotic solvents such as dimethylformamide, N-methylpyrrolidone. Also mixtures of these solvents may be used.

The reaction pressure is customarily from 0 to 6 bar. Preference is given to carrying out the reaction under atmospheric pressure. If the reaction is carried out under atmospheric pressure, the reaction temperature is customarily from 0 to 100° C., preferably from 10 to 40° C., more preferably from 15 to 30° C.

The present invention also comprises a process for the production of 2-halogenomethylphenyl acetic acid derivatives of formula I, wherein $R^2$ is methyl or ethyl, said method comprising.

a) reacting a compound of formula V with a nitrosating agent under the conditions described above, alkylating of the resulting oxime of formula IV under the conditions described above and cleavage of the obtained alkyloxime of formula II under the conditions described above, or b) reacting a compound of formula V with a nitrosating agent as described above, cleavage of the obtained oxime of formula IV as described above and subsequent alkylation of the resulting 2-halogenomethylphenyl acetic acid derivatives of formula I, wherein $R^2$ is hydrogen, as described above.

The present invention furthermore comprises a process for the production of a strobilurine fungicide selected from the group consisting of dimoxystrobin, trifloxystrobin, kresoxime-methyl, orysastrobin, said process comprising.

(1) cleavage of an alkyloxime of formula II in the presence of an alcohol of formula III and a halogenating agent selected from the group consisting of thionyl halide, oxalyl halides and mixtures of thionyl bromide and hydrobromic acid, mixtures of thionyl chloride and hydrochloric acid or mixtures of oxalyl chloride and hydrochloric acid and mixtures of oxalyl bromide and hydrobromic acid; and (2) reacting the resulting 2-halogenomethylphenyl acetic acid derivatives of formula I to the strobilurine or the respective strobilurine precursor.

The methods for producing the strobilurins mentioned above based on 2-halogenomethylphenl acetic acid derivatives are generally known to the skilled artisan.

For example, orysastrobin can be prepared using compounds of formula I in accordance with the methods described in WO 97/15552. Variations on this synthesis may easily be employed by a skilled person using the disclosure of this invention.

The strobilurines kresoxim-methyl and dimoxystrobine can be prepared using compounds of formula I by substitution reaction with the respective phenol derivative according to the methods described in WO 2008/125592 A1. Variations on this synthesis may easily be employed by a skilled person using the disclosure of this invention.

The strobilurine trifloxystrobin can be prepared using compounds of formula I by substitution with the respective 3-trifluoromethylacetophenone oxime according to the methods described in DE19508573 A and CN 1793115 A. Variations on this synthesis may easily be employed by a skilled person using the disclosure of this invention.

The invention is further illustrated but not limited by the following examples:

EXAMPLE 1

Isochroman-3,4-dione 4-oxime [Identical to 4-(Hydroxyimino)isochroman-3-one] by nitrosation of isochromanone To a suspension of isochromanone (99% pure, 149.7 g, 1.00 mol) in methanol (280 mL) was added dropwise over a period of 90 min at 14-16° C. sodium methanolate (30% in methanol, 270.0 g, 1.50 mol) and the resulting mixture was stirred for 90 min at 15° C. To this mixture was added dropwise over a period of 6.5 h at 9-13° C. iso-butyl nitrite (94% pure, 137.1 g, 1.25 mol) and the mixture was stirred at 8° C. overnight. The conversion was monitored by HPLC. After completion of the reaction, 4 M hydrochloric acid was added to adjust a pH<1 before the resulting suspension was stirred for overnight at 4° C. The crude product was collected by filtration, washed with cold dist. water (2×500 mL) and dried in vacuo at max. 45° C. Isochroman-3,4-dione-4-oxime was obtained as a colorless solid (145.9 g, 90.4 HPLC-area %, 74% yield).

$^1$H-NMR (DMSO-d6): δ=13.3 (s, 1H), 8.34 (d, J=7.4 Hz, 1H), 7.54-7.41 (m, 3H), 5.46 (s, 2H) ppm; $^{13}$C-NMR (DMSO-d6): δ=162.3, 140.2, 133.2, 130.2, 129.0, 127.9, 125.4, 125.0, 68.3 ppm; mp=179-182° C.

EXAMPLE 2

Isochroman-3,4-dione 4-(O-methyl-oxime) [identical to 4-(Methoxyimino)isochroman-3-one] by methylation of isochroman-3,4-dione 4-oxime A suspension of isochroman-3,4-dione 4-oxime (90.4 HPLC-area %, 145.8 g, 0.74 mol) and potassium carbonate (153.4 g, 1.11 mol) in toluene (1000 mL) was stirred at ambient temperature for 1 h before dimethylsulfate (141.4 g, 1.11 mol) was added dropwise at 26° C. over a period of 2.5 h. The resulting mixture was stirred for 24 h at ambient temperature. After completion of the reaction, dist. water (1000 mL) was added to the mixture under stirring. The organic layer was separated, washed with dist. water (500 mL) and dried in vacuo at 30-50 mbar and max. 50° C. Isochroman-3,4-dione 4-(O-methyl-oxime) was obtained as a light orange solid (160.1 g, 88.7 HPLC-area %, quant. yield, diastereomeric ratio=58:42).

$^1$H-NMR (CDCl$_3$, TMS as internal standard) (main isomer): δ=8.27-8.24 (m, 1H), 7.48-7.40 (m, 2H), 7.31-7.27 (m, 1H), 5.35 (s, 2H), 4.22 (s, 3H) ppm; $^{13}$C-NMR (CDCl$_3$, TMS as internal standard) (main isomer): δ=162.2, 140.5, 133.0, 131.0, 130.0, 128.4, 125.4, 124.8, 69.1, 65.5 ppm.

EXAMPLE 3

(2-Chloromethyl-phenyl)-[(E)-methoxyimino]-acetic acid methyl ester (CLMO) by addition of thionyl chloride to isochroman-3,4-dione 4-(O-methyl-oxime) in methanol To a solution of isochroman-3,4-dione 4-(O-methyl-oxime) (88.7 HPLC-area %, 160 g, 0.74 mol, diastereomeric ratio=58:42) in methanol (890 g, 27.74 mol) was added dropwise at 15-20° C. over a period of 5 h thionyl chloride (889.5 g, 7.40 mol) and the mixture was stirred overnight at ambient temperature (20-25° C.). The conversion was monitored by HPLC. After completion of the reaction, the solvent was evaporated in vacuo at 30-50 mbar and max. 55° C. The resulting residue (216 g) was dissolved in toluene (500 mL), dist. water was added (300 mL) and the mixture was stirred at ambient temperature. The phases were separated and the organic phase was evaporated in vacuo at 30-50 mbar and max. 55° C. to yield the crude product as a colorless oil (179 g, 56.7 HPLC-weight % CLMO, 54% yield). Recrystallization of the crude product from methanol (89 g) led to colorless crystals of (2-Chloromethyl-phenyl)-[(E)methoxyimino]-acetic acid methyl ester CLMO (64.7 g, 94.7 HPLC-weight %, 34% yield).

$^1$H-NMR (CDCl$_3$, TMS as internal standard): δ=7.50-7.47 (m, 1H), 7.43-7.35 (m, 2H), 7.18-7.14 (m, 1H), 4.42 (s, 2H), 4.03 (s, 3H), 3.85 (s, 3H) ppm; $^{13}$C-NMR (CDCl$_3$, TMS as internal standard): δ=163.2, 149.0, 135.5, 130.2, 129.8, 129.6, 128.6, 128.4, 63.8, 53.0, 44.0 ppm.

EXAMPLE 4

(2-Chloromethyl-phenyl)-[(E)-methoxyimino]-acetic acid methyl ester (CLMO) by addition of methanolic HCl and thionyl chloride to isochroman-3,4-dione 4-(O-methyl-oxime)

To a freshly prepared solution of gaseous HCl (21 g) in methanol (20 g) [HCl gas was inserted at −10° C.] was added dropwise at −10° C. a solution of isochroman-3,4-dione 4-(O-methyl-oxime) (89.5 HPLC-area %, 14.8 g, 0.069 mol) in methanol (82.9 g). After completion of addition, thionyl chloride (4.6 g, 38 mmol) was added dropwise below 0° C. and the resulting mixture was stirred overnight. HPLC indicated a conversion of the isochroman-3,4-dione 4-(O-methyl-oxime) >97% HPLC-area %. The solution contained (2-chloromethyl-phenyl)-[(E)-methoxyimino]-acetic acid methyl ester of 72% HPLC-area % purity. Work-up can be performed according to example 3.

EXAMPLE 5

(2-Chloromethyl-phenyl)-[(E)-methoxyimino]-acetic acid ethyl ester by addition of thionyl chloride to isochroman-3,4-dione 4-(O-methyl-oxime) in ethanol The synthesis was performed according to the procedure described in example 3 using ethanol as a solvent.

$^1$H-NMR (CDCl$_3$, TMS as internal standard): δ=7.51-7.47 (m, 1H), 7.43-7.34 (m, 2H), 7.18-7.14 (m, 1H), 4.44 (s, 2H), 4.33 (q, J=7.1 Hz, 2H), 4.04 (s, 3H), 1.32 (t, J=7.1 Hz, 3H)

ppm. $^{13}$C-NMR (CDCl$_3$, TMS as internal standard): δ=162.8, 149.3, 135.5, 130.4, 129.7, 129.6, 128.6, 128.3, 63.8, 62.2, 44.0, 14.1 ppm.

EXAMPLE 6

(2-Chloromethyl-phenyl)-[(E)-methoxyimino]-acetic acid ethyl ester by addition of addition of ethanolic HCl and thionyl chloride to isochroman-3,4-dione 4-(O-methyl-oxime)

The synthesis was performed according to the procedure described in example 4 using ethanol as a solvent.

EXAMPLE 7

(2-Bromomethyl-phenyl)-[(E)-methoxyimino]-acetic acid methyl ester (BRMO) by addition of thionyl bromide to isochroman-3,4-dione 4-(O-methyl-oxime)

To a solution of isochroman-3,4-dione 4-(O-methyl-oxime) (5.6 g, 0.028 mol) in methanol (27 g) was added dropwise at 10-20° C. thionyl bromide (45.4 g, 0.22 mol) over a period of 1 h and the resulting mixture was stirred at ambient temperature overnight. The reaction was monitored by HPLC. Concentration of the mixture in vacuo led to a crude residue (14.2 g). A small amount of the residue (3.2 g) was purified by silica column chromatography to yield (2-bromomethyl-phenyl)-[(E)-methoxyimino]-acetic acid methyl ester as a colorless solid (0.8 g).

$^1$H-NMR (CD$_2$Cl$_2$, TMS as internal standard): δ=7.50-7.46 (m, 1H), 7.43-7.35 (m, 2H), 7.16-7.12 (m, 1H), 4.34 (s, 2H), 4.02 (s, 3H), 3.83 (s, 3H) ppm; $^{13}$C-NMR (CD$_2$Cl$_2$, TMS as internal standard): δ=163.4, 149.2, 136.3, 131.1, 130.5, 130.1, 129.2, 128.8, 64.1, 53.2, 31.3 ppm.

EXAMPLE 8

(2-Chloromethyl-phenyl)-hydroxyimino-acetic acid methyl ester by addition of thionyl chloride to isochroman-3,4-dione 4-(O-methyl-oxime) in methanol and dichloromethane To a solution of isochroman-3,4-dione 4-oxime (98% pure, 3.5 g, 0.02 mol) in methanol (35 g) and dichlormethane (32 g) was added dropwise at 20-30° C. thionyl chloride (24.0 g, 0.2 mol). The resulting mixture was stirred at ambient temperature for 3 d. The reaction was monitored by HPLC. After completion of the reaction, the mixture was concentrated in vacuo and a crude residue was obtained (5.5 g). A part of this residue (5.1 g) was dissolved in MTBE and was washed with water. The mixture was concentrated and the resulting residue was purified by silica column chromatography by yield (2-chloromethyl-phenyl)-hydroxyimino-acetic acid methyl ester as a colorless solid (3.4

EXAMPLE 9

(2-Chloromethyl-phenyl)-[(E)-methoxyimino]-acetic acid methyl ester (CLMO) by methylation of (2-chloromethyl-phenyl)-hydroxyimino-acetic acid methyl ester The synthesis was performed according to the procedure described in example 2.

EXAMPLE 10

Synthesis of Orysastrobin from (2-Chloromethyl-phenyl)-[(E)methoxyimino]-acetic acid methyl ester (CLMO)

A solution of (2E,3Z,4E)-pentane-2,3,4-trione O$^2$,O$^3$-dimethyl trioxime and its (2E,3Z,4Z)-isomer (36.8% in DMF) (101.7 g, 0.200 mol) was treated at 20° C. with a solution of sodium methylate (30% in methanol) (39.5 g, 0.219 mol). After 15 min at 20 C the methanol was distilled off in vacuo at 40° C.

Afterwards, a solution of (2-Chloromethyl-phenyl)-[(E)-methoxyimino]-acetic acid methyl ester (CLMO) (45% in DMF) (113.4 g, 0.200 mol) was added to the residue at 40 to 50° C. within 15 min and the reaction mixture was stirred at 50° C. for 3 hours. For the amidation step a solution of methylamine (18.6 g, 0.600 mol) in methanol (65.7 g) was added to the mixture and the resulting reaction mixture was stirred for 3 hours at 50° C. Methylamine and methanol were then distilled off in vacuo at 50° C. After an extraction with toluene and a water wash, toluene was distilled off giving rise to 74.9 g of crude residue. The crude residue was dissolved at 50° C. in a mixture of methanol (248 g) and water (186 g) and was then cooled to −5° C. for crystallization. The resulting crystals were filtered off and were washed afterwards with a methanol/water mixture followed by a rinse with water. The solid was dried in vacuo at 70° C. yielding 48.5 g of a solid that contained 95% of the EEE-isomer of Orysastrobin and 4.5% of its EEZ-isomer.

$^1$H-NMR (CD$_2$Cl$_2$, TMS as internal standard) (main isomer): δ=7.41-6.95 (m, 4H), 5.03 (s, 2H), 3.89 (s, 3H), 3.88 (s, 3H), 3.86 (s, 3H), 2.76 (d, J=5.0 Hz, 3H), 1.97 (s, 3H), 1.86 (s, 3H) ppm; $^{13}$C-NMR (CD$_2$Cl$_2$, TMS as internal standard) (main isomer): δ=163.0, 153.7, 152.2, 151.5, 150.7, 136.0, 130.8, 129.2, 129.2, 129.2, 128.0, 76.0, 63.3, 63.2, 61.9, 26.2, 14.7, 10.3 ppm; mp=95-96° C.

The invention claimed is:

1. A process for producing a compound of formula (I)

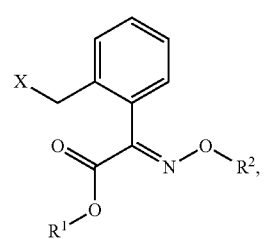

wherein X is chlorine or bromine,
R$^1$ is methyl, ethyl, n-propyl or i-propyl; and
R$^2$ is methyl or ethyl;
said process comprising providing a compound of formula (II)

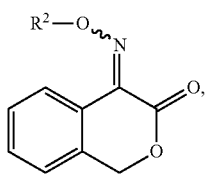
(II)

wherein
R$^2$ is methyl or ethyl;
and cleaving the compound of formula (II) in the presence of a compound of formula (III)

R$^1$—OH (III), and a halogenating agent selected from the group consisting of thionyl halide, oxalyl halides and mixtures of thionyl bromide and hydrobromic acid, mixtures of thionyl chloride and hydrochloric acid, mixtures of oxalyl chloride and hydrochloric acid or mixtures of oxalyl bromide and hydrobromic acid;
to obtain a compound of formula (I).

2. The process of claim 1, wherein R$^1$ is methyl or ethyl.

3. The process of claim 1, wherein the halogenating agent is thionyl halide.

4. The process of claim 1, wherein the halogenating agent is a mixture of thionyl chloride and hydrochloric acid or thionyl bromide and hydrobromic acid.

5. A process for the production of a compound of formula (II),

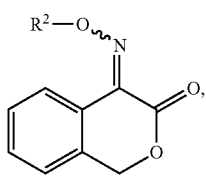
(II)

wherein R$^2$ is methyl or ethyl, said process comprising reacting a compound of formula (IV)

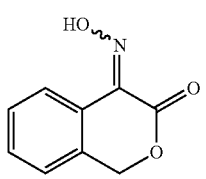
(IV)

with an alkylating agent and a base in an inert organic solvent, wherein the inert organic solvent is toluene;
to obtain a compound of formula (II).

6. The process of claim 1,
wherein said providing of a compound of formula (II) comprises providing a compound of formula (IV)

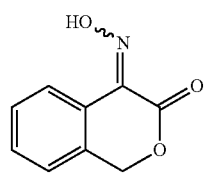
(IV)

and reacting the compound of formula (IV) with an alkylating agent and a base in an inert organic solvent, wherein the inert organic solvent is toluene to yield a compound of formula (II).

7. A process for producing a compound of formula (IV)

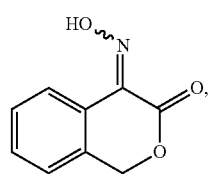
(IV)

comprising a) reacting a compound of formula (V)

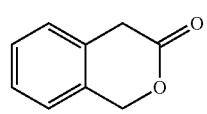
(V)

with a nitrosating agent in the presence of an alcohol and a base; and b) after completion of the reaction adjusting the pH to a pH ≤3.

8. The process of claim 6, wherein said providing of a compound of formula (IV) comprises providing a compound of formula (V)

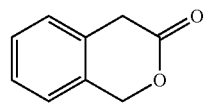
(V)

and reacting the compound of formula (V) with a nitrosating agent in the presence of an alcohol and a base; and c) after completion of the reaction adjusting the pH to a pH ≤3.

9. A process for producing a compound of formula (I)

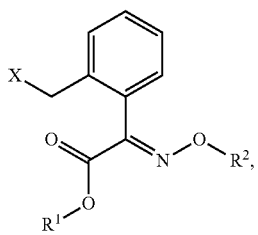
(I)

wherein $R^2$ is methyl or ethyl; and
X is chlorine or bromine;
comprising reacting a compound of formula I, wherein $R^2$ is hydrogen with an alkylating agent in an inert organic solvent.

10. A process for producing a compound of formula I, comprising
a) reacting a compound of formula (V)

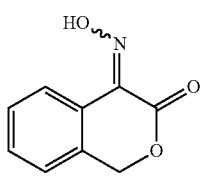
(V)

with a nitrosating agent in presence of an alcohol and a base; and
after completion of the reaction adjusting the pH to a pH ≤3;
reacting the resulting compound of formula (IV)

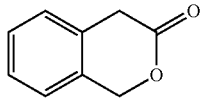
(IV)

with an alkylating agent and a base in an inert organic solvent, wherein the inert organic solvent is toluene to yield a compound of formula (II);

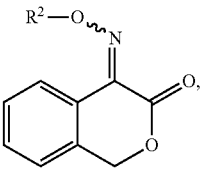
(II)

wherein $R^2$ is methyl or ethyl;
and cleaving the compound of formula (II) in the presence of a compound of formula (III)

$R^1$—OH (III), or
b) reacting a compound of formula (V) with a nitrosating agent in the presence of an alcohol and a base; and
after completion of the reaction adjusting the pH to a pH ≤3 to yield a compound of formula (IV);
cleaving the compound of formula (IV) in the presence of a compound of formula (III)

$R^1$—OH (III), and alkylating the resulting 2-halogenomethylphenyl acetic acid derivatives of formula I

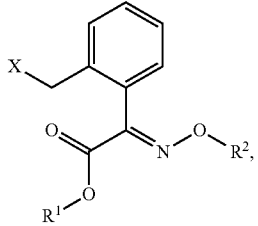
(I)

wherein $R^2$ is hydrogen, and X is chlorine or bromine;
to the 2-halogenomethylphenyl acetic acid derivatives of formula I, wherein $R^2$ is ethyl or methyl.

* * * * *